US00PP16498P2

(12) United States Plant Patent
Zary

(10) Patent No.: US PP16,498 P2
(45) Date of Patent: May 2, 2006

(54) GRANDIFLORA ROSE PLANT NAMED 'JACTOURN'

(50) Latin Name: *Rosa hybrida*
Varietal Denomination: JACtourn

(75) Inventor: Keith W. Zary, Agoura Hills, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 54 days.

(21) Appl. No.: 10/969,257

(22) Filed: Oct. 19, 2004

(51) Int. Cl.
*A01H 5/00* (2006.01)

(52) U.S. Cl. ..... Plt./140

(58) Field of Classification Search ..... Plt./139, Plt./140
See application file for complete search history.

(56) References Cited

U.S. PATENT DOCUMENTS

PP11,293 P * 3/2000 Zary ..... Plt./139

* cited by examiner

*Primary Examiner*—Howard J. Locker
(74) *Attorney, Agent, or Firm*—Klarquist Sparkman LLP

(57) ABSTRACT

Grandiflora rose plant having large, well-formed flowers of dark red, non-fading flower color; large, glossy foliage; resistance to powdery mildew and rust; and ease of propagation by softwood cuttings.

1 Drawing Sheet

Genus and species: *Rosa hybrida.*
Variety denomination: 'JACtourn'.

ORIGIN OF THE INVENTION

The present invention relates to a new and distinct variety of a shrub rose plant named 'JACtourn' which was originated by me by crossing the variety 'JACient' (U.S. Plant Pat. No. 6,725), with the variety 'MACtrum' (U.S. Plant Pat. No. 4,297).

BACKGROUND OF THE INVENTION

The primary objective of this breeding was to produce a new rose variety having the large flowers, glossy, healthy foliage and large clusters of the female parent combined with the profuse flowering, bright flower color and glossy, healthy foliage of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from other varieties of which I am aware:

1. Large, well-formed flowers.
2. Dark red, non-fading flower color.
3. Large, glossy foliage.
4. Resistance to powdery mildew and rust.
5. Ease of propagation by softwood cuttings.

Asexual reproduction of this new variety by cuttings, as performed at Wasco, Calif., shows that the foregoing and all other characteristics and distinctions come true to form and are established and transmitted through succeeding propagations.

Comparison with Parents

As compared to the female parent 'JACient' which has light coral pink flowers, 'JACtourn' is similar in flower size but has dark red flowers. The male parent 'MACtrum' has orange red flowers.

Comparison with Similar Variety

'JACtourn' compares best in flower color to 'JACzor' but has larger flowers, larger foliage and longer stems.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:
*Seed parent.*—'JACient', U.S. Plant Pat. No. 6,725.
*Pollen parent.*—'MACtrum', U.S. Plant Pat. No. 4,297.

FLOWER

Observations made of plants commencing at four years of age in a garden environment at Somis, Calif., from January 2003 to August 2004.

Blooming habit: Continuous.
Bud:
*Size.*—About 5 cm long and 4 cm in diameter when the petals start to unfurl.

*Form.*—The bud is long, pointed ovoid.

*Color.*—When sepals first divide, bud color is Red Group 45B. When half blown, the upper sides of the petals are Red Group 46B and the lower sides of the petals are Red Group 46B.

*Sepals.*—Color: Upper surface: Green Group 138B. Lower surface: Green Group 137D. Length: 35 mm. Width: 11 mm. Shape: Subulate. Surface texture: Upper: Hoary; Lower: Glaborous. There are three normally appendaged sepals. There are two unappendaged sepals with hairy edges.

*Receptacle.*—Color: Green Group 137B often with areas of Greyed-Purple Group 183C where exposed to bright sunlight. Shape: Funnel. Size: Medium, about 10 mm long×12 mm wide. Surface: Smooth.

*Peduncle.*—Length: Medium, averaging about 7 cm. Surface: Smooth with a few glands. Color: Green Group 137D. Strength: Stiff, erect.

Bloom:

*Size.*—Large. Average open diameter is about 12 cm.

*Borne.*—Singly or several together in flat clusters of 3–5 blooms.

*Stems.*—Strength: Strong. Average length is about 45 cm with a diameter of 5–6 mm.

*Form.*—When first open: High centered. Permanence: Retains its form to the end, outer petals curl back.

*Petalage.*—Number of petals under normal conditions: 35.

*Color.*—The upper sides of the petals are Red Group 46B. The reverse sides of the petals are Red Group 46B. The base of each petal has a small 3 mm×3 mm Yellow-Green Group 154D color spot. The major color on the upper side is Red Group 46B.

*Variegations.*—None observed.

*Discoloration.*—The general tonality at the end of the first day: No change. At the end of the third day: No change. Further aging: When petals are close to dropping (day 5 or 6), color changes slightly to Red Group 46C.

*Fragrance.*—Slight, spicy.

Petals:

*Texture.*—Thick.

*Shape.*—Round to deltoid.

*Surface.*—Smooth.

*Margin.*—Smooth and entire. Apex Shape: Obtuse. Base Shape: Rounded.

*Form.*—Tips slightly recurved.

*Arrangement.*—Imbricated.

*Petaloids.*—Number: 1–3. Size: Length — 3 to 5 mm. Width — 2 to 3 mm. Color: Red Group 46B.

*Persistence.*—Petals drop off cleanly before drying.

*Lastingness.*—On the plant: Long (about 5–6 days). As a cut flower: Long (about 7–8 days).

Reproductive parts:

*Stamens.*—Number: 80–100. Length: 12 mm. Anthers: Length: 3 mm. Color: Yellow-Orange Group 22A. Arrangement: Regular around styles. Filaments: Color: Red Group 42A. Length: 9 mm. Pollen: Color: Yellow-Orange Group 23C.

*Pistils.*—Number: 70–90. Length: 5–8 mm. Styles: Color: Yellow-White Group 158D at the base, gradually changing to Red Group 43A at apex. Length: 4–7 mm. Stigmas: Color: Orange-White Group 159B. Length: 1 mm.

*Hips.*—None observed.

PLANT

*Form.*—Bush.

*Growth.*—Vigorous, upright, branching.

*Age at maturity.*—Two years.

*Mature plant.*—Height: 150 cm. Width: 80cm.

*Rootstock.*—Own root.

Foliage: Number of leaflets on normal mid-stem leaves: 5 or 7.

*Size.*—Large. About 16 cm long×14 cm wide.

*Quality.*—Abundant.

*Color.*—New foliage: Upper side: Greyed-Purple Group 183B. Lower side: Greyed-Purple Group 183D. Old foliage: Upper side: Green Group 137A. Lower side: Green Group 137D.

Leaflets:

*Size.*—About 55–60 mm long×35–40 mm wide.

*Shape.*—Broadly oval.

*Base shape.*—Rounded.

*Apex shape.*—Acuminate.

*Texture.*—Leathery, glossy, coriacious.

*Edge.*—Serrated.

*Serrations.*—Single.

*Petiole.*—Color: Yellow-Green Group 145B.

*Petiole rachis.*—Color: Yellow-Green Group 145B. Underside: Smooth.

*Stipules.*—Length: 26–28 mm.

*Disease resistance.*—Resistant to mildew and rust and susceptible to blackspot under normal growing conditions.

*Pest resistance.*—Not observed.

*Vein color.*—Yellow-Green Group 145B.

*Venation pattern.*—Reticulate.

Wood:

*New wood.*—Color: Greyed-Purple Group 183B. Bark: Smooth.

*Old wood.*—Color: Green Group 137B. Bark: Smooth.

Prickles:

*Quantity.*—On main canes from base: About 14 prickles per 15 cm stem. On laterals from main canes: About 14 prickles per 15 cm stem.

*Form.*—Hooked downward.

*Length.*—7 mm.

*Color when young.*—Greyed-Purple Group 183B.

*Color when mature.*—Greyed-Orange Group 165A.

Small prickles:

*Quantity.*—On main stalks: None. On laterals: None.

Winter hardiness: Hardy to Zone 5.

I claim:

1. A new and distinct variety of rose plant of the grandiflora class, substantially as herein shown and described, characterized particularly by its large, well-formed flowers of dark red, non-fading flower color; large, glossy foliage; resistance to powdery mildew and rust; and ease of propagation by softwood cuttings.

* * * * *

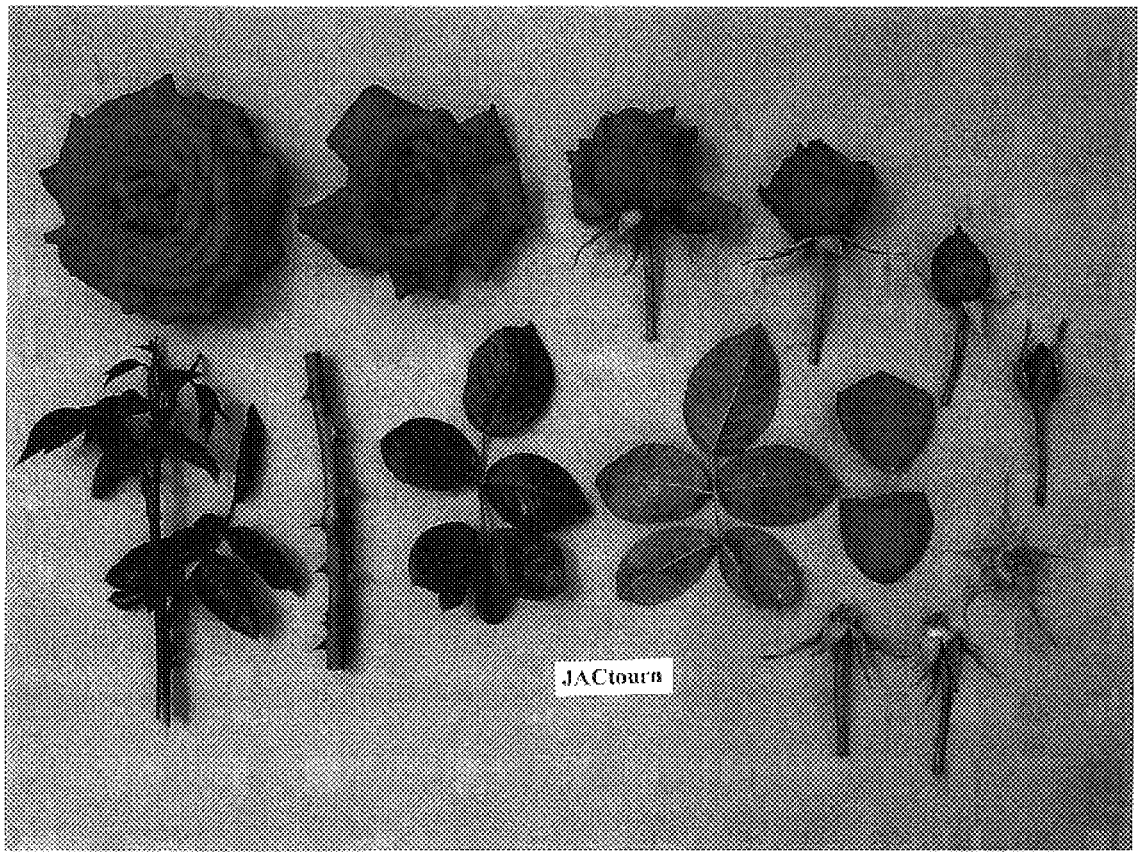
JACtours